United States Patent
Perkins et al.

(10) Patent No.: US 9,733,183 B2
(45) Date of Patent: Aug. 15, 2017

(54) DESIGNS FOR INTEGRATED COMPUTATIONAL ELEMENTS

(71) Applicant: Halliburton Energy Services, Inc., Houston, TX (US)

(72) Inventors: David L. Perkins, The Woodlands, TX (US); Robert Paul Freese, Pittsboro, NC (US); Christopher Michael Jones, Houston, TX (US); Richard Neal Gardner, Raleigh, NC (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 173 days.

(21) Appl. No.: 14/413,376

(22) PCT Filed: Feb. 20, 2014

(86) PCT No.: PCT/US2014/017309
§ 371 (c)(1),
(2) Date: Jan. 7, 2015

(87) PCT Pub. No.: WO2015/126396
PCT Pub. Date: Aug. 27, 2015

(65) Prior Publication Data
US 2016/0274027 A1    Sep. 22, 2016

(51) Int. Cl.
*G01N 21/45*    (2006.01)
*G02B 5/28*    (2006.01)
*G01N 21/85*    (2006.01)

(52) U.S. Cl.
CPC ............. *G01N 21/45* (2013.01); *G02B 5/28* (2013.01); *G02B 5/285* (2013.01); *G01N 21/85* (2013.01);

(Continued)

(58) Field of Classification Search
CPC ................ G02B 5/285; G01N 21/45
See application file for complete search history.

(56) References Cited

U.S. PATENT DOCUMENTS 4,770,496 A * 9/1988 Mahlein ............... G02B 5/285
                                                        359/588
5,549,953 A * 8/1996 Li ...................... G02B 5/285
                                                        369/283

(Continued)

FOREIGN PATENT DOCUMENTS

WO    2013162799 A1    10/2013
WO    2015126396 A1    8/2015

OTHER PUBLICATIONS

International Search Report and Written Opinion for PCT/US2014/017309 dated Nov. 18, 2014.

*Primary Examiner* — Michael A Lyons
(74) *Attorney, Agent, or Firm* — McDermott Will & Emery LLP (57) ABSTRACT

Disclosed are improved integrated computational elements for use in optical computing devices. One integrated computational element includes an optical substrate, first and second pluralities of optical thin film layers alternatingly deposited on the optical substrate to form a thin film stack, wherein each optical thin film layer of the first plurality exhibits a first refractive index and each optical thin film layer of the second plurality exhibits a second refractive index different than the first refractive index, and at least one additional optical thin film layer arranged in or on the thin film stack and in optical communication with at least one of the optical thin film layers of the first and second pluralities, the at least one additional optical thin film layer exhibiting a third refractive index that is different than the first and second refractive indices.

22 Claims, 3 Drawing Sheets

(52) U.S. Cl.
CPC . *G01N 2201/061* (2013.01); *G01N 2201/068* (2013.01); *G01N 2201/12* (2013.01); *G01N 2201/129* (2013.01)

(56) References Cited

U.S. PATENT DOCUMENTS

| | | | |
|---|---|---|---|
| 6,198,531 B1* | 3/2001 | Myrick | G01J 3/28 |
| | | | 356/213 |
| 6,239,876 B1* | 5/2001 | Brandenberg | G01N 21/45 |
| | | | 356/481 |
| 6,926,410 B2 | 8/2005 | Weber et al. | |
| 7,138,156 B1 | 11/2006 | Myrick et al. | |
| 7,880,966 B2 | 2/2011 | Suzuki | |
| 7,901,870 B1* | 3/2011 | Wach | G02B 5/285 |
| | | | 430/321 |
| 8,184,371 B2 | 5/2012 | Myrick | |
| 2005/0141093 A1* | 6/2005 | Weber | G02B 5/287 |
| | | | 359/584 |
| 2006/0055308 A1* | 3/2006 | Lairson | G02B 5/284 |
| | | | 313/489 |
| 2006/0142955 A1* | 6/2006 | Jones | E21B 47/102 |
| | | | 702/32 |
| 2012/0065948 A1* | 3/2012 | Tan | G01J 3/28 |
| | | | 703/2 |
| 2013/0034842 A1 | 2/2013 | Tunheim et al. | |
| 2013/0284900 A1 | 10/2013 | Freese et al. | |

\* cited by examiner

DESIGNS FOR INTEGRATED COMPUTATIONAL ELEMENTS

This application is a national stage entry of and claims priority to International Application No. PCT/US2014/17309, filed on Feb. 20, 2014 entitled Improved Designs for Integrated Computational Elements.

BACKGROUND

The present invention relates to optical computing devices and, more particularly, to improved optical processing elements for use in optical computing devices.

Optical computing devices, also commonly referred to as "opticoanalytical devices," can be used to analyze and monitor a sample substance in real time. Such optical computing devices will often employ a light source that emits electromagnetic radiation that reflects from or is transmitted through the sample and optically interacts with an optical processing element to determine quantitative and/or qualitative values of one or more physical or chemical properties of the substance being analyzed. The optical processing element may be, for example, an integrated computational element (ICE). One type of an ICE is an optical thin film interference device, also known as a multivariate optical element (MOE). Each ICE can be designed to operate over a continuum of wavelengths in the electromagnetic spectrum from the UV to mid-infrared (MIR) ranges, or any sub-set of that region. Electromagnetic radiation that optically interacts with the sample substance is changed and processed by the ICE so as to be measured by a detector. The output of the detector can be correlated to a physical or chemical property of the substance being analyzed.

A traditional ICE (hereafter "ICE core") includes first and second pluralities of optical thin film layers consisting of various materials whose index of refraction and size (e.g., thickness) varies between each layer. An ICE core design refers to the substrate, number and thickness of the respective layers of the ICE core, and the refractive indices of the layers. The layers may be strategically deposited and sized so as to selectively pass predetermined fractions of electromagnetic radiation at different wavelengths configured to substantially mimic a regression vector corresponding to a particular physical or chemical property of interest of a substance of interest. Accordingly, an ICE core design will exhibit a transmission function that is weighted with respect to wavelength. As a result, the output light intensity from the ICE core conveyed to the detector may be related to the physical or chemical property of interest for the substance.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present invention relates to optical computing devices and, more particularly, to improved optical processing elements for use in optical computing devices.

The present disclosure expands the design palate for optical processing elements, such as integrated computational elements ("ICE cores"), for use in optical computing devices. Whereas traditional ICE cores are made up of alternating first and second pluralities of optical thin film layers, the embodiments disclosed herein include ICE designs having one or more additional optical thin film layers in addition to the first and second alternating pluralities. The additional layer(s) may exhibit a refractive index that is different than the refractive indices exhibited by the first and second pluralities of layers and thereby increase the tolerance associated with a given single optical thin film layer and also increase the flexibility of designing an ICE core for a given application. In some embodiments, the additional optical thin film layer may be a terminal layer deposited on the stack of the first and second pluralities of optical thin film layers. In such embodiments, the additional or "terminal" layer may provide a protective layer for the ICE core and otherwise be deposited to correct any defects or errors in the deposition process of the first and second pluralities of optical thin film layers.

The embodiments disclosed herein provide optical processing elements (e.g., ICE cores) that may be used in the oil and gas industry, such as for monitoring and detecting oil/gas-related substances (e.g., hydrocarbons, drilling fluids, completion fluids, treatment fluids, etc.). It will be appreciated, however, that the ICE cores may equally be used in other technology fields including, but not limited to, the food industry, the paint industry, the mining industry, the agricultural industry, the medical and pharmaceutical industries, the automotive industry, the cosmetics industry, water treatment facilities, and any other field where it may be desired to monitor substances in real time.

As used herein, the term "characteristic" or "characteristic of interest" refers to a chemical, mechanical, or physical property of a substance or a sample of the substance. The characteristic of a substance may include a quantitative or qualitative value of one or more chemical constituents or compounds present therein or any physical property associated therewith. Such chemical constituents and compounds may be referred to herein as "analytes." Illustrative characteristics of a substance that can be analyzed with the help of the optical processing elements described herein can include, for example, chemical composition (e.g., identity and concentration in total or of individual components), phase presence (e.g., gas, oil, water, etc.), impurity content, pH, alkalinity, viscosity, density, ionic strength, total dissolved solids, salt content (e.g., salinity), porosity, opacity, bacteria content, total hardness, transmittance, state of matter (solid, liquid, gas, emulsion, mixtures thereof, etc.), and the like.

As used herein, the term "substance," or variations thereof, refers to at least a portion of matter or material of interest to be tested or otherwise evaluated with the help of the optical processing elements described herein. The substance may be any fluid capable of flowing, including particulate solids, liquids, gases (e.g., air, nitrogen, carbon dioxide, argon, helium, methane, ethane, butane, and other hydrocarbon gases, hydrogen sulfide, and combinations thereof), slurries, emulsions, powders, muds, glasses, mixtures, combinations thereof, and may include, but is not limited to, aqueous fluids (e.g., water, brines, etc.), non-aqueous fluids (e.g., organic compounds, hydrocarbons, oil, a refined component of oil, petrochemical products, and the like), acids, surfactants, biocides, bleaches, corrosion inhibitors, foamers and foaming agents, breakers, scavengers, stabilizers, clarifiers, detergents, treatment fluids, fracturing fluids, formation fluids, or any oilfield fluid, chemical, or substance commonly found in the oil and gas industry. The substance may also refer to solid materials such as, but not limited to, rock formations, concrete, solid wellbore surfaces, pipes or flow lines, and solid surfaces of any wellbore tool or projectile (e.g., balls, darts, plugs, etc.).

As used herein, the term "electromagnetic radiation" refers to radio waves, microwave radiation, terahertz, infrared and near-infrared radiation, visible light, ultraviolet light, X-ray radiation and gamma ray radiation.

As used herein, the phrase "optically interact" or variations thereof refers to the reflection, transmission, scattering, diffraction, or absorption of electromagnetic radiation either on, through, or from an optical processing element (e.g., an integrated computational element) or a substance being analyzed with the help of the optical processing element. Accordingly, optically interacted light refers to electromagnetic radiation that has been reflected, transmitted, scattered, diffracted, or absorbed by, emitted, or re-radiated, for example, using an optical processing element, but may also apply to optical interaction with a substance.

As used herein, the term "optical computing device" refers to an optical device that is configured to receive an input of electromagnetic radiation associated with a substance and produce an output of electromagnetic radiation from an optical processing element arranged within or otherwise associated with the optical computing device. The optical processing element may be, for example, an integrated computational element (ICE). The electromagnetic radiation that optically interacts with the optical processing element is changed so as to be readable by a detector, such that an output of the detector can be correlated to a particular characteristic of the substance being analyzed. The output of electromagnetic radiation from the optical processing element can be reflected, transmitted, and/or dispersed electromagnetic radiation. Whether the detector analyzes reflected, transmitted, or dispersed electromagnetic radiation may be dictated by the structural parameters of the optical computing device as well as other considerations known to those skilled in the art. In addition, emission and/or scattering of the fluid, for example via fluorescence, luminescence, Raman, Mie, and/or Raleigh scattering, can also be monitored by optical computing devices.

As indicated above, the present disclosure provides or otherwise describes improved optical processing elements, such as an integrated computational element (ICE core), for use in optical computing devices. In operation, an ICE core is capable of distinguishing electromagnetic radiation related to a characteristic of interest of a substance from electromagnetic radiation related to other components of the substance.

Figure 1:
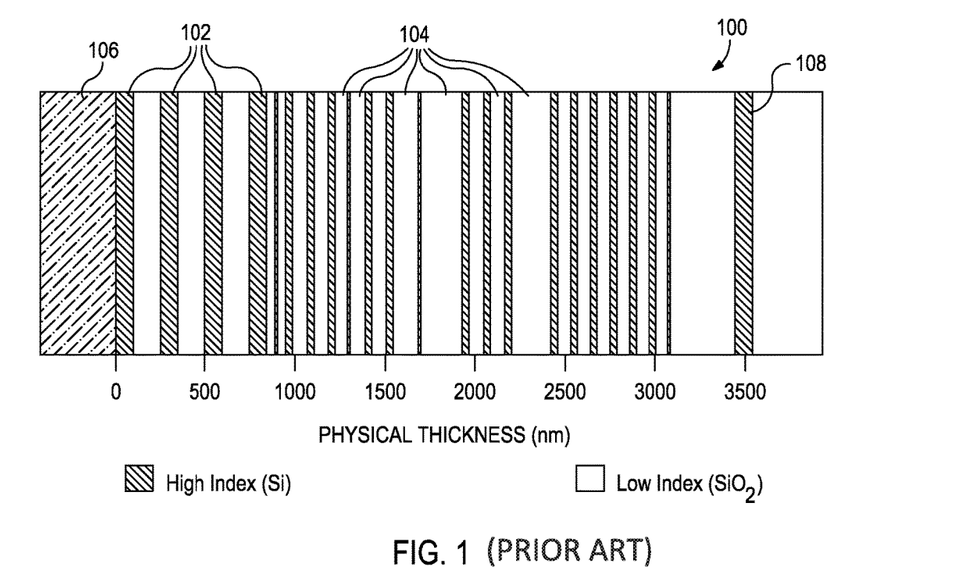
FIG. 1 illustrates a traditional integrated computation element, according to one or more embodiments of the present disclosure.

Referring to FIG. 1, illustrated is a traditional ICE core 100. As illustrated, the traditional ICE core 100 includes a plurality of alternating thin film layers shown as layers 102 and 104. The first layers 102 are made of a material that exhibits a high index of refraction, such as silicon (Si), and the second layers 104 are made of a material that exhibits a low index of refraction, such as quartz ($SiO_2$). Other examples of materials that might be used include, but are not limited to, niobia and niobium, germanium and germania, MgF, SiO, and other high and low index materials generally known in the art. Yet other examples of materials that might be used include new technology polymers that exhibit high or low indices of refraction such as, but not limited to, low index fluoropolymers and high index nano-particle filled polymers (organic and inorganic matrix materials). It should be noted that, as used herein, the terms "refractive index," "refractive indices," "index of refraction," and any variation thereof refers to the complex refractive index that includes both the real and imaginary (absorptive) parts thereof. The layers 102, 104 are strategically deposited on an optical substrate 106, such as BK-7 optical glass. In other embodiments, the substrate 106 may be another type of optical substrate, such as another optical glass, silica, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the substrate 106 in FIG. 1), the traditional ICE core 100 may include a layer 108 that is generally exposed to the environment of the device or installation. The number of layers 102, 104 and the thickness of each layer 102, 104 are determined from the spectral attributes acquired from a spectroscopic analysis of a characteristic of the substance being analyzed using a conventional spectroscopic instrument. The spectrum of interest of a given characteristic typically includes any number of different wavelengths.

It should be understood that the ICE core 100 depicted in FIG. 1 does not in fact represent any particular ICE core configured to detect a specific characteristic of a given substance, but is provided for purposes of illustration only. Consequently, the number of layers 102, 104 and their relative thicknesses, as shown in FIG. 1, bear no correlation to any particular substance or characteristic thereof. Nor are the layers 102, 104 and their relative thicknesses necessarily drawn to scale, and therefore should not be considered limiting of the present disclosure.

In some embodiments, the material of each layer 102, 104 can be doped or two or more materials can be combined in a manner to achieve the desired optical characteristic. In addition to solids, the ICE core 100 may also contain liquids and/or gases, optionally in combination with solids, in order to produce a desired optical characteristic. In at least one embodiment, for example, one of the second layers 104 may be an air gap that acts as a potential low index material. In other embodiments, the liquid may be sol-gel, for example. In the case of gases and liquids, the ICE core 100 can contain a corresponding vessel (not shown), which houses the gases or liquids. Exemplary variations of the ICE core 100 may also include holographic optical elements, gratings, piezoelectric, light pipe, and/or acousto-optic elements, for example, that can create transmission, reflection, and/or absorptive properties of interest.

The multiple layers 102, 104 may exhibit different refractive indices. By properly selecting the materials of the layers 102, 104 and their relative thickness and spacing, the ICE core 100 will be configured to selectively transmit or reflect predetermined fractions of electromagnetic radiation at different wavelengths. Each wavelength is given a predetermined weighting or loading factor. The thickness and spacing of the layers 102, 104 may be determined using a variety of approximation methods from the spectrum of the characteristic or analyte of interest. These methods may include inverse Fourier transform (IFT) of the optical transmission spectrum and structuring the ICE core 100 as the physical representation of the IFT. The approximations convert the IFT into a structure based on known materials with constant refractive indices.

The weightings that the layers 102, 104 of the ICE core 100 apply at each wavelength are set to the regression weightings described with respect to a known equation, or data, or spectral signature. For instance, when electromagnetic radiation interacts with a substance, unique physical and chemical information about the substance is encoded in the electromagnetic radiation that is reflected from, transmitted through, or radiated from the substance. This information is often referred to as the spectral "fingerprint" of the substance. The ICE core 100 is configured to perform the dot product of the received electromagnetic radiation and the wavelength dependent transmission function of the ICE core 100. The wavelength dependent transmission function of the ICE core 100 is dependent on the substrate, the material refractive index of each layer, the number of layers 102, 104 and thickness of each layer 102, 104. As a result, the output light intensity of the ICE core 100 is related to the characteristic or analyte of interest.

As further explanation, accurately determining the regression vector of the characteristic of interest in the sample substance provides a means for an optical computing device to determine or otherwise calculate a concentration of said characteristic in the sample substance. The regression vector for each characteristic may be determined using standard procedures that will be familiar to one having ordinary skill in the art. For example, analyzing the spectrum of the sample substance may include determining a dot product of the regression vector for each characteristic of the sample substance being analyzed. As one of ordinary skill in art will recognize, a dot product of a vector is a scalar quantity (i.e., a real number). While the dot product value is believed to have no physical meaning by itself (e.g., it may return a positive or negative result of any magnitude), comparison of the dot product value of a sample substance with dot product values obtained for known reference standards and plotted in a calibration curve may allow the sample substance dot product value to be correlated with a concentration or value of a characteristic, thereby allowing unknown sample substances to be accurately analyzed.

To determine the dot product, one multiples the regression coefficient of the regression vector at a given wavelength by the spectral intensity at the same wavelength. This process is repeated for all wavelengths analyzed, and the products are summed over the entire wavelength range to yield the dot product. Those skilled in the art will recognize that two or more characteristics may be determined from a single spectrum of the sample substance by applying a corresponding regression vector for each characteristic.

In practice, it is possible to derive information from electromagnetic radiation interacting with a sample substance by, for example, separating the electromagnetic radiation from several samples into wavelength bands and performing a multiple linear regression of the band intensity against a characteristic of interest determined by another measurement technique for each sample substance. The measured characteristic may be expressed and modeled by multiple linear regression techniques that will be familiar to one having ordinary skill in the art. Specifically, if y is the measured value of the concentration or characteristic, y may be expressed as in Equation 1:

$$y = a_0 + a_1 w_1 + a_2 w_2 + a_3 w_3 + a_4 w_4 + \ldots \quad \text{Equation (1)}$$

where each 'a' is a constant determined by the regression analysis and each 'w' is the light intensity for each wavelength band. Depending on the circumstances, the estimate obtained from Equation (1) may be inaccurate, for example, due to the presence of other characteristics within the sample substance that may affect the intensity of the wavelength bands. A more accurate estimate may be obtained by expressing the electromagnetic radiation in terms of its principal components.

To obtain the principal components, spectroscopic data is collected for a variety of similar sample substances using the same type of electromagnetic radiation. For example, following exposure to each sample substance, the electromagnetic radiation may be collected and the spectral intensity at each wavelength may be measured for each sample substance. This data may then be pooled and subjected to a linear-algebraic process known as singular value decomposition (SVD) in order to determine the principal components. Use of SVD in principal component analysis will be well understood by one having ordinary skill in the art. Briefly, however, principal component analysis is a dimension reduction technique that takes 'm' spectra with 'n' independent variables and constructs a new set of eigenvectors that are linear combinations of the original variables. The eigenvectors may be considered a new set of plotting axes. The primary axis, termed the first principal component, is the vector that describes most of the data variability. Subsequent principal components describe successively less sample variability, until the higher order principal components essentially describe only spectral noise.

Typically, the principal components are determined as normalized vectors. Thus, each component of an electromagnetic radiation sample may be expressed as $x_n z_n$, where $x_n$ is a scalar multiplier and $z_n$ is the normalized component vector for the $n^{th}$ component. That is, $z_n$ is a vector in a multi-dimensional space where each wavelength is a dimension. Normalization determines values for a component at each wavelength so that the component maintains its shape and the length of the principal component vector is equal to one. Thus, each normalized component vector has a shape and a magnitude so that the components may be used as the basic building blocks of any electromagnetic radiation sample having those principal components. Accordingly, each electromagnetic radiation sample may be described by a combination of the normalized principal components multiplied by the appropriate scalar multipliers, as set forth in Equation (2):

$$x_1 z_1 + x_2 z_2 + \ldots + x_n z_n \quad \text{Equation (2)}$$

The scalar multipliers $x_n$ may be considered the "magnitudes" of the principal components in a given electromagnetic radiation sample when the principal components are understood to have a standardized magnitude as provided by normalization.

Because the principal components are orthogonal, they may be used in a relatively straightforward mathematical procedure to decompose an electromagnetic radiation sample into the component magnitudes, which may accurately describe the data in the original electromagnetic radiation sample. Since the original electromagnetic radiation sample may also be considered a vector in the multi-dimensional wavelength space, the dot product of the original signal vector with a principal component vector is the magnitude of the original signal in the direction of the normalized component vector. That is, it is the magnitude of the normalized principal component present in the original signal. This is analogous to breaking a vector in a three dimensional Cartesian space into its X, Y and Z components. The dot product of the three-dimensional vector with each axis vector, assuming each axis vector has a magnitude of 1, gives the magnitude of the three dimensional vector in each of the three directions. The dot product of the original signal and some other vector that is not perpendicular to the other three dimensions provides redundant data, since this magnitude is already contributed by two or more of the orthogonal axes.

Because the principal components are orthogonal to each other, the dot product of any principal component with any other principal component is zero. Physically, this means that the components do not spectrally interfere with each other. If data is altered to change the magnitude of one component in the original electromagnetic radiation signal, the other components remain unchanged. In the analogous Cartesian example, reduction of the X component of the three dimensional vector does not affect the magnitudes of the Y and Z components.

Principal component analysis provides the fewest orthogonal components that can accurately describe the data carried by the electromagnetic radiation samples. Thus, in a mathematical sense, the principal components are components of the original electromagnetic radiation that do not interfere with each other and that represent the most compact description of the spectral signal. Physically, each principal component is an electromagnetic radiation signal that forms a part of the original electromagnetic radiation signal. Each principal component has a shape over some wavelength range within the original wavelength range. Summing the principal components may produce the original signal, provided each component has the proper magnitude, whether positive or negative.

The principal components may comprise a compression of the information carried by the total light signal. In a physical sense, the shape and wavelength range of the principal components describe what information is in the total electromagnetic radiation signal, and the magnitude of each component describes how much of that information is present. If several electromagnetic radiation samples contain the same types of information, but in differing amounts, then a single set of principal components may be used to describe (except for noise) each electromagnetic radiation sample by applying appropriate magnitudes to the components. The principal components may be used to provide an estimate of the characteristic of the sample substance based upon the information carried by the electromagnetic radiation that has interacted with that sample substance. Differences observed in spectra of sample substances having varying quantities of an analyte or values of a characteristic may be described as differences in the magnitudes of the principal components. Thus, the concentration of the characteristic may be expressed by the principal components according to Equation (3) in the case where four principal components are used:

$$y = a_0 + a_1 x_1 + a_2 x_2 + a_3 x_3 + a_4 x_4 \quad \text{Equation (3)}$$

where 'y' is a concentration or value of a characteristic, each a is a constant determined by the regression analysis, and $x_1$, $x_2$, $x_3$ and $x_4$ are the first, second, third, and fourth principal component magnitudes, respectively. Equation (3) may be referred to as a regression vector. The regression vector may be used to provide an estimate for the concentration or value of the characteristic for an unknown sample.

Regression vector calculations may be performed by computer, based on spectrograph measurements of electromagnetic radiation by wavelength. The spectrograph system spreads the electromagnetic radiation into its spectrum and measures the spectral intensity at each wavelength over the wavelength range. Using Equation (3), the computer may read the intensity data and decompose the electromagnetic radiation sample into the principal component magnitudes $x_n$ by determining the dot product of the total signal with each component. The component magnitudes are then applied to the regression equation to determine a concentration or value of the characteristic.

To simplify the foregoing procedure, however, the regression vector may be converted to a form that is a function of wavelength so that only one dot product is determined. Each normalized principal component vector $z_n$ has a value over all or part of the total wavelength range. If each wavelength value of each component vector is multiplied by the regression constant and corresponding to the component vector, and if the resulting weighted principal components are summed by wavelength, the regression vector takes the form of Equation (4):

$$y = a_0 + b_1 u_1 + b_2 u_2 + \ldots + b_n u_n \quad \text{Equation (4)}$$

where $a_0$ is the first regression constant from Equation (3), $b_n$ is the sum of the multiple of each regression constant $a_n$ from Equation (3) and the value of its respective normalized regression vector at wavelength 'n', and $u_n$ is the intensity of the electromagnetic radiation at wavelength 'n'. Thus, the new constants define a vector in wavelength space that directly describes a concentration or characteristic of a sample substance. The regression vector in the form of Equation (4) represents the dot product of an electromagnetic radiation sample with this vector.

Normalization of the principal components provides the components with an arbitrary value for use during the regression analysis. Accordingly, it is very unlikely that the dot product value produced by the regression vector will be equal to the actual concentration or characteristic value of a sample substance being analyzed. The dot product result is, however, related (e.g., proportional or having a logarithmic or exponential relationship) to the concentration or characteristic value. As discussed above, the relationship may be determined by measuring one or more known calibration samples by conventional means and comparing the result to the dot product value of the regression vector. Thereafter, the dot product result can be compared to the value obtained from the calibration standards in order to determine the concentration or characteristic of an unknown sample being analyzed.

Still referring to FIG. 1, the traditional ICE core 100 has historically been made of only two pluralities of alternating optical thin film layers 102, 104 made of different materials; one material that exhibits a high index of refraction (e.g., silicon), and a second material that exhibits a low index of refraction (e.g., silicon dioxide). According to the present disclosure, however, improvements to traditional ICE cores may be obtained by introducing to the stack of layers 102, 104 at least one additional optical thin film layer that exhibits a refractive index different than the refractive indices exhibited by the first and second pluralities of layers 102, 104. As will be appreciated by those skilled in the art, the addition of one or more layers may prove advantageous in increasing the tolerance associated with a given single layer, thereby also increasing the flexibility of designing an ICE core for a given application. As a result, the manufacturing process to achieve a viable ICE core, or an ICE core that is more accurate, may be made easier.

Figure 2:
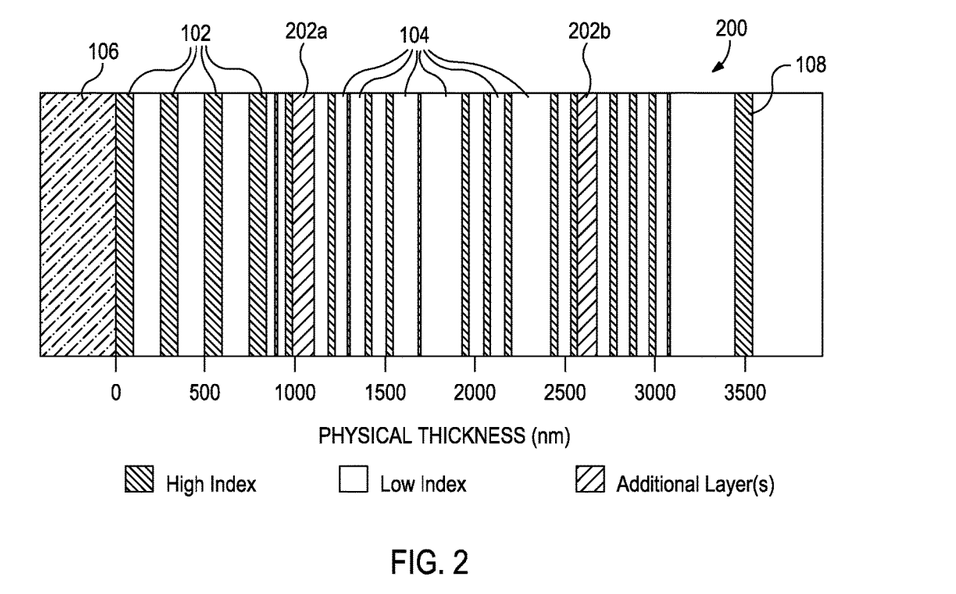
FIG. 2 illustrates an exemplary integrated computational element, according to one or more embodiments of the present disclosure.

Referring now to FIG. 2, with continued reference to FIG. 1, illustrated is an exemplary integrated computational element 200, according to one or more embodiments of the present disclosure. Similar to the traditional ICE core 100 of FIG. 1, the integrated computational element 200 (hereafter "ICE core 200") may include the first and second pluralities of alternating optical thin film layers 102 and 104 deposited on an optical substrate 106. Moreover, the first layers 102 may be made of a material that exhibits a high index of refraction and the second layers 104 may be made of a material that exhibits a low index of refraction. For example, layers 102 may be Si and have a nominal refractive index of 3.6, whereas layers 104 may be $SiO_2$ and have a nominal refractive index of 1.5. Suitable materials for the first and second pluralities of layers 102, 104 and the substrate 106 are discussed above and therefore will not be provided again.

As will be appreciated by those skilled in the art, whether a material exhibits a "high" index of refraction is relative to materials that exhibit a "low" index of refraction. In other words, it may be less important how high or low the index of refraction is for a particular material, but rather the difference between the refractive indices of neighboring layers made of differing materials. For instance, and not to limit the present disclosure, a refractive index mismatch of 0.2 between a "high" substance (e.g., glass), which exhibits a refractive index of 1.5, and a low substance (e.g., aqueous substance) which exhibits a refractive index of 1.3, may be more useful or suitable than a 0.1 difference between germanium (i.e., refractive index of 4.0) and doped germanium (i.e., refractive index of 3.9) even though the latter refractive indices are higher than the former.

Unlike the traditional ICE core 100 of FIG. 1, however, the ICE core 200 may further include at least one additional or third type of optical thin film layer 202 (shown as additional layers 202a and 202b) deposited on the substrate 106 and otherwise interposing adjacent layers 102, 104 at one or more locations along the stack. In the illustrated embodiment, the ICE core 200 includes two additional layers 202a and 202b deposited at specific locations along the stack of layers 102, 104 extending from the substrate 106. It will be appreciated, however, that other embodiments of the ICE core 200 may include more or less than two additional layers 202a,b (including a single additional layer 202), and the additional layers 202a,b may be deposited or otherwise arranged in any other location along the stack of layers 102, 104, without departing from the scope of the disclosure.

The additional layer(s) 202a,b may be made of a material that exhibits a refractive index that is different than the respective refractive indices of the first and second pluralities of layers 102, 104. More particularly, one or more of the additional layers 202a,b may be made of a material such as, but not limited to, silicon (Si), quartz ($SiO_2$), $SiO_X$, niobia and niobium, germanium and germania, MgF, zinc oxide, $TiO_2$, $Al_2O_3$, tantalum and tantalum oxide, low index fluoropolymers, high index nano-particle filled polymers (organic and inorganic matrix materials), and any other material generally known in the art to exhibit a refractive index.

In some embodiments, the material of the additional layer(s) 202a,b may be doped or two or more materials can be combined in a manner to achieve a desired refractive index for the additional layer(s) 202a,b. In other embodiments, one or more of the additional layers 202a,b may be made of a liquid and/or a gas contained within corresponding containment vessels (not shown) configured to house the gas and/or liquid between adjacent layers 102, 104. In yet other embodiments, one or more of the additional layers 202a,b may be made of a gas or liquid in combination with one of the solids mentioned above.

It should be understood that the ICE core 200 depicted in FIG. 2 does not in fact represent any particular ICE core design for detecting a specific characteristic of a given substance, but is provided for purposes of illustration only. Consequently, the number of layers 102, 104, 202a,b and their relative thicknesses, as shown in FIG. 2, bear no correlation to any particular substance or characteristic thereof. Nor are the layers 102, 104, 202a,b and their relative thicknesses necessarily drawn to scale, and therefore should not be considered limiting of the present disclosure.

In some embodiments, the refractive index of the additional layer(s) 202 may be greater than the refractive index of the first plurality of layers 102. In other embodiments, the refractive index of the layer(s) 202 may be close to but slightly offset from the refractive index of the first plurality of layers 102; i.e., a refractive index value that is slightly above or below the refractive index of the first plurality of layers 102. In yet other embodiments, the value of the refractive index of the layer(s) 202 may generally lie between the corresponding refractive indices of the first and second pluralities of layers 102, 104; e.g., a "medium" refractive index, for example 2.6. In other embodiments, the refractive index of the additional layer(s) 202 may be close but slightly offset from the refractive index of the second plurality of layers 104; i.e., a refractive index value that is slightly above or below the refractive index of the second plurality of layers 104. In yet other embodiments, the refractive index of the additional layer(s) 202 may be less than the refractive index of the second plurality of layers 104.

In one example, the additional layer 202 may be generally made of the same material as an adjacent one of the first and second pluralities of layers 102, 104. In such embodiments, however, the additional layer 202 may nonetheless exhibit a refractive index that is different than the adjacent layers 102, 104. Such may be the case where the material of adjacent layers (i.e., an additional layer 202 and either one of the layers 102, 104) is $SiO_X$. In such cases, the addition of oxygen during the deposition process of the additional layer(s) 202 adjusts or modifies the resulting refractive index, thereby allowing the user to fine-tune the ICE core 200 to achieve desired accuracies. It has been found that adding oxygen atoms in ratios between $SiO_1$ and $SiO_2$, for example, can alter the refractive index of the material. Such may also be the case with all the oxide families, where the oxygen stoichiometry will change the complex index of refraction and oxygen content can be controlled during the deposition process by adding known quantities to the vacuum during deposition.

As will be appreciated, other materials may equally be added during the deposition process in order to alter the refractive index of the additional layer(s) 202. For example, metal ions, such as tin or indium, may be added to the layer(s) 202 during the deposition process to modify or otherwise tune the refractive index of the additional layer(s) 202, without departing from the scope of the disclosure.

Since the multiple layers 102, 104, 202a,b exhibit different refractive indices, it may be possible to strategically select the materials of the layers 102, 104, 202a,b (and their relative thickness and spacing) such that the ICE core 200 will be configured to selectively transmit or reflect predetermined fractions of electromagnetic radiation at different wavelengths. As a result, the ICE core 200 may be better able to accurately determine the characteristic or analyte of interest being measured in a sample substance.

Moreover, while the ICE core 200 is shown as including one or more additional layers 202a,b, embodiments are contemplated herein that include one or more extra-additional layers (not shown) in addition to the layers 102, 104, 202a,b. In such embodiments, the extra-additional layer(s) may exhibit a refractive index that is different than the first and second pluralities of layers 102, 104, and/or different than the additional layer(s) 202a,b, without departing from the scope of the disclosure.

Figure 3:
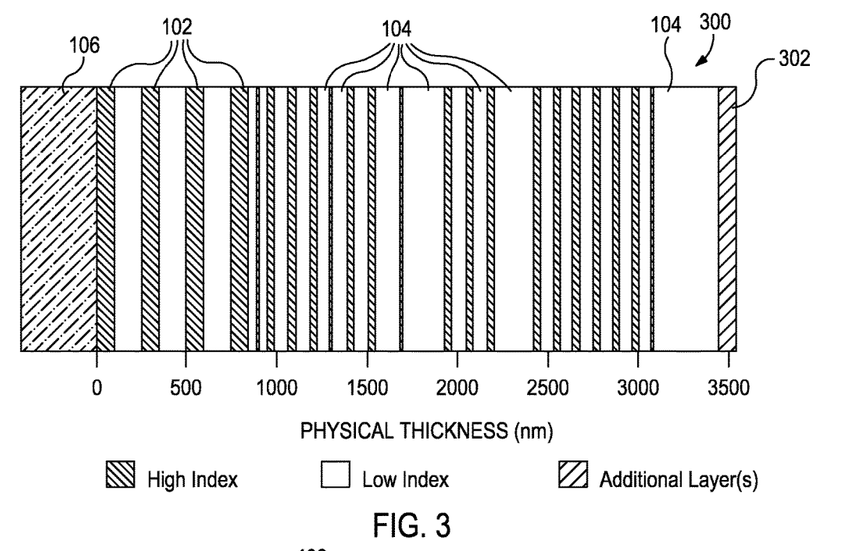
FIG. 3 illustrates an exemplary integrated computational element, according to one or more embodiments of the present disclosure.

Referring now to FIG. 3, with continued reference to FIGS. 1 and 2, illustrated is another exemplary integrated computational element 300, according to one or more embodiments of the present disclosure. Similar to the traditional ICE core 100 of FIG. 1, the integrated computational element 300 (hereafter "ICE 300") may include the first and second pluralities of alternating optical thin film layers 102 and 104 deposited on an optical substrate 106. Moreover, the first layers 102 may be made of a material that exhibits a high index of refraction and the second layers 104 may be made of a material that exhibits a low index of refraction. For example, as mentioned above, layers 102 may be Si and have a nominal refractive index of 3.6, whereas layers 104 may be $SiO_2$ and have a nominal refractive index of 1.5. Other suitable materials for the first and second pluralities of layers 102, 104 and the substrate 106 are discussed above and therefore will not be provided again.

Unlike the traditional ICE core 100 of FIG. 1, however, the ICE core 300 may further include at least one additional or terminal optical thin film layer(s) 302 deposited on the end of the stack of layers 102, 104 extending from the substrate 106. In the illustrated embodiment, the ICE core 300 includes a single terminal optical thin film layer 302 but, in other embodiments, may include more than two terminal layers 302, without departing from the scope of the disclosure. Moreover, the terminal layer 302 is depicted in FIG. 3 as being deposited on one of the second plurality of layers 104, but may equally be deposited on one of the first plurality of layers 102, without departing from the scope of the disclosure, and depending on the particular ICE design.

The additional layer 302 may be made of a material such as, but not limited to, silicon (Si), quartz ($SiO_2$), $SiO_x$, niobia and niobium, germanium and germania, MgF, zinc oxide, $TiO_2$, $Al_2O_3$, tantalum and tantalum oxide, low index fluoropolymers, high index nano-particle filled polymers (organic and inorganic matrix materials), and other materials generally known in the art to exhibit refractive indices. In general, most oxides and refractory oxides would be a suitable material for the additional layer 302. Moreover, the material of the additional layer 302 may be doped or two or more of the above-referenced materials can be combined in a manner to achieve a desired refractive index for the additional layer 302. In other embodiments, the terminal layer 302 may be made of a liquid and/or a gas contained within a corresponding containment vessel (not shown) configured to house the gas and/or liquid. In yet other embodiments, the terminal layer 302 may be made of a gas or liquid in combination with one of the solids mentioned above.

Similar to the additional layer(s) 202a,b of FIG. 2, the additional or terminal layer 302 may be made of a material that exhibits a refractive index that is different than that of the first and second pluralities of layers 102, 104. In some embodiments, for instance, the materials of the first and second pluralities of layers 102, 104 and the terminal layer 302 may be different. In other embodiments, however, the additional layer 302 may be generally made of the same material as an adjacent one of the first and second pluralities of layers 102, 104 but nonetheless exhibit a refractive index that is different than the adjacent first and second pluralities of layers 102, 104. As discussed above, this may be accomplished by adding additional oxygen atoms or metal ions to the layer 302 during the deposition process to modify the refractive index of the terminal layer 302.

In some embodiments, the refractive index of the additional or terminal layer 302 may be greater than the refractive index of the first plurality of layers 102. In other embodiments, the refractive index of the layer(s) 302 may be close to but slightly offset from the refractive index of the first plurality of layers 102; i.e., a refractive index value that is slightly above or below the refractive index of the first plurality of layers 102. In yet other embodiments, the value of the refractive index of the layer(s) 302 may lie between the refractive indices of the first and second pluralities of layers 102, 104; e.g., a "medium" refractive index, for example 2.6. In other embodiments, the refractive index of the additional layer(s) 302 may be close but slightly offset from the refractive index of the second plurality of layers 104; i.e., a refractive index value that is slightly above or below the refractive index of the second plurality of layers 104. In yet other embodiments, the refractive index of the additional layer(s) 302 may be less than the refractive index of the second plurality of layers 104.

The additional or terminal layer(s) 302 may be added to the stack of layers 102, 104 during a separate deposition step or process configured to optically correct or modify the final optical transmission function of the ICE core 300 design. In such embodiments, once the ICE core 300 is fabricated, it may be tested to determine how well it performs. Errors in the deposition process may have resulted in the ICE core 300 not performing as well as it was designed to. In such embodiments, one or more terminal layers 302 may be added to the stack of layers 102, 104 to improve the performance of the ICE core 300. According to the present disclosure, the terminal layer(s) 302 may exhibit a predetermined refractive index and thickness configured to increase the sensitivity of the ICE core 300.

In some embodiments, the additional or terminal layer(s) 302 may be used as a protective layer to the stack of layers 102, 104. In such embodiments, the terminal layer(s) 302 may be made of a harder material, such as an oxide (e.g., titanium oxide), a refractory oxide, a nitride (e.g., boron nitride), a refractory nitride, a carbide (e.g., tantalum, titanium, tungsten, silicon, etc.), a refractory carbide, and any combination thereof. The harder material may prove advantageous in protecting the ICE core 300 from damage during operation, such as being scratched, or otherwise prevent the ICE core 300 from the inadvertent separation of layers 102, 104. The harder material may also prove advantageous in making the ICE core 300 more environmentally stable or otherwise inert to environmental conditions, such as extreme chemical and/or thermal environments. In some embodiments, the material of the terminal layer 302 may be non-conductive. Such properties may prove advantageous in applications where the ICE core 300 is in contact with the sample substance being measured. Accordingly, the terminal layer 302 may be configured to make the ICE core 300 more robust for long-term operation.

In at least one embodiment, the terminal layer 302 may be made of a material that exhibits an index of refraction that is substantially similar to its adjacent or previous layer 102, 104. In such embodiments, the refractive index mismatch described above may be observed between the environment (i.e., air) adjacent the terminal layer 302 and the combined terminal layer 302 and adjacent layer 102, 104. As a result, the surrounding air may technically serve as the final layer to the ICE core 300. Accordingly, it may prove advantageous in capping the stack of layers 102, 104 with a more environmentally-stable or hard compound, even though such a terminal layer 302 may exhibit the same or substantially similar index of refraction as the previous layer 102, 104.

Figure 4:
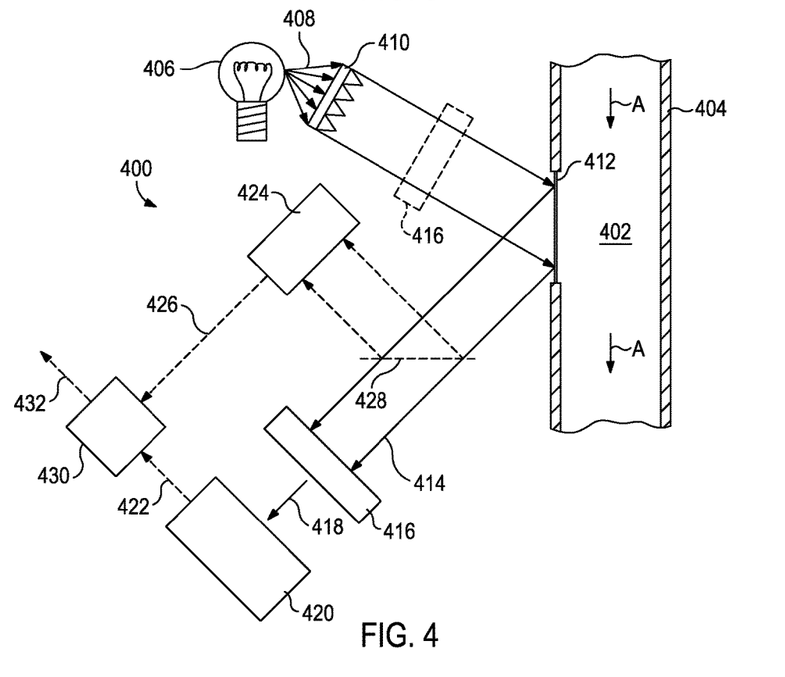
FIG. 4 illustrates an exemplary optical computing device for monitoring a substance, according to one or more embodiments.

Referring now to FIG. 4, illustrated is an exemplary optical computing device 400 for monitoring a substance 402, according to one or more embodiments. In the illustrated embodiment, the substance 402 may be a fluid contained or otherwise flowing within an exemplary flow path 404. The flow path 404 may be a flow line, a pipeline, a wellbore, an annulus defined within a wellbore, or any flow lines or pipelines extending to/from a wellbore. The substance 402 present within the flow path 404 may be flowing in the general direction indicated by the arrows A (i.e., from upstream to downstream). As will be appreciated, however, the flow path 404 may be any other type of flow path, such as a mud pit (i.e., used for drilling fluids and the like) or any other containment or storage vessel, and the substance 402 may not necessarily be flowing in the direction A while the substance 402 is being monitored.

The optical computing device 400 may be configured to determine a characteristic of interest in the substance 402 or a component present within the substance 402. In some embodiments, the device 400 may include an electromagnetic radiation source 406 configured to emit or otherwise generate electromagnetic radiation 408. The electromagnetic radiation source 406 may be any device capable of emitting or generating electromagnetic radiation, as defined herein. For example, the electromagnetic radiation source 406 may be a light bulb, a light emitting diode (LED), a laser, a blackbody, a photonic crystal, an X-Ray source, combinations thereof, or the like. In some embodiments, a lens 410 may be configured to collect or otherwise receive the electromagnetic radiation 408 and direct a beam 214 of electromagnetic radiation 408 toward the substance 402. The lens 410 may be any type of optical device configured to transmit or otherwise convey the electromagnetic radiation 408 as desired, such as a normal lens, a Fresnel lens, a diffractive optical element, a holographic graphical element, a mirror (e.g., a focusing mirror), or a type of collimator. In other embodiments, the lens 410 may be omitted from the device 400 and the electromagnetic radiation 408 may instead be directed toward the substance 402 directly from the electromagnetic radiation source 406.

In one or more embodiments, the device 400 may also include a sampling window 412 arranged adjacent to or otherwise in contact with the substance 402 for detection purposes. The sampling window 412 may be made from a variety of transparent, rigid or semi-rigid materials that are configured to allow transmission of the electromagnetic radiation 408 therethrough. For example, the sampling window 412 may be made of, but is not limited to, glasses, plastics, semi-conductors, crystalline materials, polycrystalline materials, hot or cold-pressed powders, combinations thereof, or the like. After passing through the sampling window 412, the electromagnetic radiation 408 impinges upon and optically interacts with the substance 402, including any components present within the substance 402. As a result, optically interacted radiation 414 is generated by and reflected from the substance 402. Those skilled in the art, however, will readily recognize that alternative variations of the device 400 may allow the optically interacted radiation 414 to be generated by being transmitted, scattered, diffracted, absorbed, emitted, or re-radiated by and/or from the substance 402, without departing from the scope of the disclosure.

The optically interacted radiation 414 generated by the interaction with the substance 402 may be directed to or otherwise be received by an ICE core 416 arranged within the device 400. The ICE core 416 may be similar to one of the ICE cores 200 and 300 described herein above. Accordingly, the ICE core 416 may include first and second pluralities of optical thin film layers exhibiting high and low refractive indices, respectively, and one or more additional optical thin film layers that exhibit a refractive index different than that of the first and second pluralities of optical thin film layers. In operation, the ICE core 416 may be configured to receive the optically interacted radiation 414 and produce modified electromagnetic radiation 418 corresponding to a particular characteristic of the substance 402. In particular, the modified electromagnetic radiation 418 is electromagnetic radiation that has optically interacted with the ICE core 416, whereby an approximate mimicking of the regression vector corresponding to the characteristic of the substance 402 is obtained.

While FIG. 4 depicts the ICE core 416 as receiving reflected electromagnetic radiation from the substance 402, the ICE core 416 may be arranged at any point along the optical train of the device 400, without departing from the scope of the disclosure. For example, in one or more embodiments, the ICE core 416 (as shown in dashed) may be arranged within the optical train prior to the sampling window 412 and equally obtain substantially the same results. In other embodiments, the ICE core 416 may generate the modified electromagnetic radiation 418 through reflection, instead of transmission therethrough.

Moreover, while only one ICE core 416 is shown in the device 400, embodiments are contemplated herein which include the use of at least two ICE cores in the device 400 configured to cooperatively determine the characteristic of interest in the substance 402. For example, two or more ICE may be arranged in series or parallel within the device 400 and configured to receive the optically interacted radiation 414 and thereby enhance sensitivities and detector limits of the device 400. In other embodiments, two or more ICE cores may be arranged on a movable assembly, such as a rotating disc or an oscillating linear array, which moves such that individual ICE cores are able to be exposed to or otherwise optically interact with electromagnetic radiation for a distinct brief period of time.

In some embodiments, it may be desirable to monitor more than one characteristic of interest at a time using the device 400. In such embodiments, various configurations for multiple ICE cores can be used, where each ICE core is configured to detect a particular and/or distinct characteristic of interest. In some embodiments, the characteristic can be analyzed sequentially using multiple ICE cores that are provided a single beam of electromagnetic radiation being reflected from or transmitted through the substance 402. In some embodiments, multiple ICE cores can be arranged on a rotating disc, where the individual ICE cores are only exposed to the beam of electromagnetic radiation for a short time. Advantages of this approach can include the ability to analyze multiple characteristics of the substance 402 using a single optical computing device 400 and the opportunity to assay additional characteristics simply by adding additional ICE cores to the rotating disc.

In other embodiments, multiple optical computing devices can be placed at a single location along the flow path 404, where each optical computing device contains a unique ICE that is configured to detect a particular characteristic of interest in the substance 402. In such embodiments, a beam splitter can divert a portion of the electromagnetic radiation being reflected by, emitted from, or transmitted through the substance 402 and into each optical computing device. Each optical computing device, in turn, can be coupled to a corresponding detector or detector array that is configured to detect and analyze an output of electromagnetic radiation from the respective optical computing device. Parallel configurations of optical computing devices can be particularly beneficial for applications that require low power inputs and/or no moving parts.

Those skilled in the art will appreciate that any of the foregoing configurations can further be used in combination with a series configuration in any of the present embodiments. For example, two optical computing devices having a rotating disc with a plurality of ICE cores arranged thereon can be placed in series for performing an analysis at a single location along the length of the flow path 404. Likewise, multiple detection stations, each containing optical computing devices in parallel, can be placed in series for performing a similar analysis.

The modified electromagnetic radiation 418 generated by the ICE core 416 may subsequently be conveyed to a detector 420 for quantification of the signal. The detector 420 may be any device capable of detecting electromagnetic radiation, and may be generally characterized as an optical transducer. In some embodiments, the detector 420 may be, but is not limited to, a thermal detector such as a thermopile or photoacoustic detector, a semiconductor detector, a piezoelectric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 420 may be configured to produce an output signal 422 in real-time or near real-time in the form of a voltage (or current) that corresponds to the particular characteristic of interest in the substance 402. The voltage returned by the detector 420 is essentially the dot product of the optical interaction of the optically interacted radiation 414 with the respective ICE core 416 as a function of the concentration of the characteristic of interest of the substance 402. As such, the output signal 422 produced by the detector 420 and the concentration of the characteristic may be related, for example, directly proportional. In other embodiments, however, the relationship may correspond to a polynomial function, an exponential function, a logarithmic function, and/or a combination thereof.

In some embodiments, the device 400 may include a second detector 424, which may be similar to the first detector 420 in that it may be any device capable of detecting electromagnetic radiation. The second detector 424 may be used to detect radiating deviations stemming from the electromagnetic radiation source 406. Undesirable radiating deviations can occur in the intensity of the electromagnetic radiation 408 due to a wide variety of reasons and potentially causing various negative effects on the device 400. These negative effects can be particularly detrimental for measurements taken over a period of time. In some embodiments, radiating deviations can occur as a result of a build-up of film or material on the sampling window 412 which has the effect of reducing the amount and quality of light ultimately reaching the first detector 420. Without proper compensation, such radiating deviations could result in false readings and the output signal 422 would no longer be primarily or accurately related to the characteristic of interest.

To compensate for these types of undesirable effects, the second detector 424 may be configured to generate a compensating signal 426 generally indicative of the radiating deviations of the electromagnetic radiation source 406, and thereby normalize the output signal 422 generated by the first detector 420. As illustrated, the second detector 424 may be configured to receive a portion of the optically interacted radiation 414 via a beamsplitter 428 in order to detect the radiating deviations. In other embodiments, however, the second detector 424 may be arranged to receive electromagnetic radiation from any portion of the optical train in the device 400 in order to detect the radiating deviations, without departing from the scope of the disclosure.

In some applications, the output signal 422 and the compensating signal 426 may be conveyed to or otherwise received by a signal processor 430 communicably coupled to both the detectors 420, 424. The signal processor 430 may be a computer including a processor and a machine-readable storage medium having instructions stored thereon, which, when executed by the processor 430, cause the optical computing device 400 to perform a number of operations, such as determining a characteristic of interest of the substance 402. For instance, the concentration of each characteristic detected with the optical computing device 400 can be fed into an algorithm operated by the signal processor 430. The algorithm can be part of an artificial neural network configured to use the concentration of each detected characteristic in order to evaluate the overall characteristic(s) or quality of the substance 402.

The signal processor 430 may also be configured to computationally combine the compensating signal 426 with the output signal 422 in order to normalize the output signal 422 in view of any radiating deviations detected by the second detector 424. Computationally combining the output and compensating signals 422, 426 may entail computing a ratio of the two signals 422, 426. For example, the concentration or magnitude of each characteristic determined using the optical computing device 400 can be fed into an algorithm run by the signal processor 430. The algorithm may be configured to make predictions on how the characteristics of the substance 402 change if the concentrations of one or more components or additives are changed relative to one another.

In real-time or near real-time, the signal processor 430 may be configured to provide a resulting output signal 432 corresponding to a concentration of the characteristic of interest in the substance 402. The resulting output signal 432 may be readable by an operator who can consider the results and make proper adjustments or take appropriate action, if needed, based upon the measured concentrations of components or additives in the substance 402. In some embodiments, the resulting signal output 328 may be conveyed, either wired or wirelessly, to an operator for consideration. In other embodiments, the resulting output signal 432 may be recognized by the signal processor 430 as being within or without a predetermined or preprogrammed range of suitable operation and may alert the operator of an out of range reading so appropriate corrective action may be taken, or otherwise autonomously undertake the appropriate corrective action such that the resulting output signal 432 returns to a value within the predetermined or preprogrammed range of suitable operation.

Figure 5:
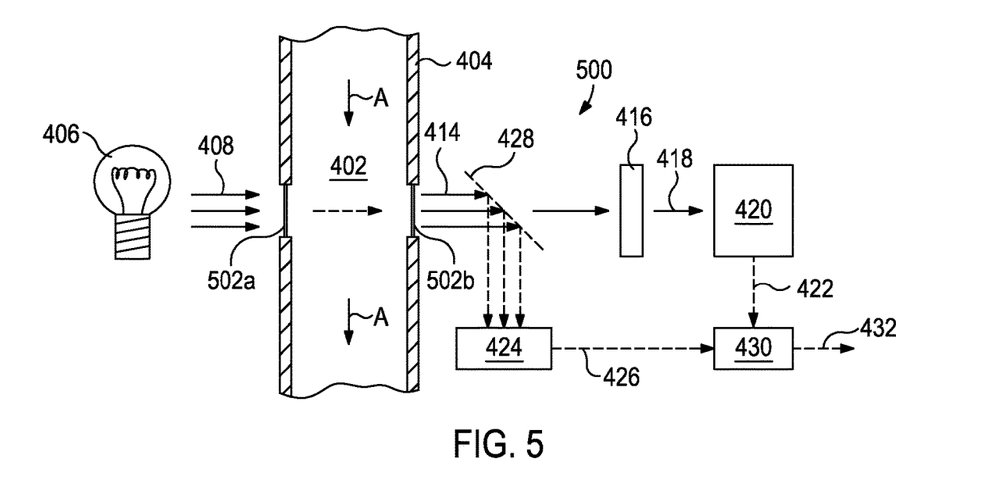
FIG. 5 illustrates another exemplary optical computing device for monitoring a substance, according to one or more embodiments.

Referring now to FIG. 5, illustrated is another exemplary optical computing device 500 for monitoring the substance 402, according to one or more embodiments. The optical computing device 500 may be similar in some respects to the optical computing device 400 of FIG. 4, and therefore may be best understood with reference thereto where like numerals indicate like elements that will not be described again. Again, the optical computing device 500 may be configured to determine the concentration of a characteristic of interest in the substance 402 as contained within the flow path 404. Unlike the device 400 of FIG. 4, however, the optical computing device 500 in FIG. 5 may be configured to transmit the electromagnetic radiation 408 through the substance 402 via a first sampling window 502a and a second sampling window 502b arranged radially-opposite the first sampling window 502a on the flow path 404. The first and second sampling windows 502a,b may be similar to the sampling window 412 described above in FIG. 4 and therefore will not be described again.

As the electromagnetic radiation 408 passes through the substance 402 via the first and second sampling windows 502a,b, it optically interacts with the substance 402 and optically interacted radiation 414 is subsequently directed to or otherwise received by the ICE core 416 as arranged within the device 500. It is again noted that, while FIG. 5 depicts the ICE core 416 as receiving the optically interacted radiation 414 as transmitted through the sampling windows 502a,b, the ICE core 416 may equally be arranged at any point along the optical train of the device 500, without departing from the scope of the disclosure. For example, in one or more embodiments, the ICE core 416 may be arranged within the optical train prior to the first sampling window 502a and equally obtain substantially the same results. In yet other embodiments, the ICE core 416 may generate the modified electromagnetic radiation 418 through reflection, instead of transmission therethrough. Moreover, as with the device 400 of FIG. 4, embodiments are contemplated herein which include the use of at least two ICE cores in the device 500 configured to cooperatively determine the characteristic of interest in the substance 402.

The modified electromagnetic radiation 418 generated by the ICE core 416 is subsequently conveyed to the detector 420 for quantification of the signal and generation of the output signal 422 which corresponds to the particular characteristic of interest in the substance 402. The device 500 may also include the second detector 424 for detecting radiating deviations stemming from the electromagnetic radiation source 406. As illustrated, the second detector 424 may be configured to receive a portion of the optically interacted radiation 414 via the beamsplitter 428 in order to detect the radiating deviations. The output signal 422 and the compensating signal 426 may then be conveyed to or otherwise received by the signal processor 430 which may computationally combine the two signals 230, 226 and provide in real-time or near real-time the resulting output signal 432 corresponding to the concentration of the characteristic of interest in the substance 402.

It should also be noted that the various drawings provided herein are not necessarily drawn to scale nor are they, strictly speaking, depicted as optically correct as understood by those skilled in optics. Instead, the drawings are merely illustrative in nature and used generally herein in order to supplement understanding of the systems and methods provided herein. Indeed, while the drawings may not be optically accurate, the conceptual interpretations depicted therein accurately reflect the exemplary nature of the various embodiments disclosed.

Embodiments disclosed herein include:

A. An integrated computational element that includes an optical substrate, first and second pluralities of optical thin film layers alternatingly deposited on the optical substrate to form a thin film stack, wherein each optical thin film layer of the first plurality exhibits a first refractive index and each optical thin film layer of the second plurality exhibits a second refractive index different than the first refractive index, and at least one additional optical thin film layer arranged in or on the thin film stack and in optical communication with at least one of the optical thin film layers of the first and second pluralities, the at least one additional optical thin film layer exhibiting a third refractive index that is different than the first and second refractive indices.

B. An optical computing device that includes a light source configured to emit electromagnetic radiation that optically interacts with a substance and an integrated computational element (ICE) core and thereby generate optically interacted light, the ICE core comprising an optical substrate, first and second pluralities of optical thin film layers alternatingly deposited on the optical substrate to form a thin film stack, wherein each optical thin film layer of the first plurality exhibits a first refractive index and each optical thin film layer of the second plurality exhibits a second refractive index different than the first refractive index, and at least one additional optical thin film layer arranged in or on the thin film stack and in optical communication with at least one of the optical thin film layers of the first and second pluralities, the at least one additional optical thin film layer exhibiting a third refractive index different than the first and second refractive indices, and at least one detector arranged to receive the optically interacted light and generate an output signal corresponding to a characteristic of the substance.

C. A method of fabricating an integrated computational element that includes alternatingly depositing first and second pluralities of optical thin film layers on an optical substrate and thereby forming a thin film stack, wherein each optical thin film layer of the first plurality exhibits a first refractive index and each optical thin film layer of the second plurality exhibits a second refractive index different than the first refractive index, and depositing at least one additional optical thin film layer in or on the thin film stack and in optical communication with at least one of the optical thin film layers of the first and second pluralities, the at least one additional optical thin film layer exhibiting a third refractive index different than the first and second refractive indices.

Each of embodiments A, B, and C may have one or more of the following additional elements in any combination: Element 1: wherein the at least one additional optical thin film layer is placed in the thin film stack between a first optical thin film layer and a second optical thin film layer. Element 2: wherein the at least one additional optical thin film layer is placed on the thin film stack as a terminal layer deposited opposite the substrate. Element 3: wherein the at least one additional optical thin film layer is made of a material selected from the group consisting of silicon (Si), quartz ($SiO_2$), $SiO_X$, niobia and niobium, germanium and germania, MgF, zinc oxide, aluminum oxide, titanium oxide, tantalum, tantalum oxide, low index fluoropolymers, and high index nano-particle filled polymers. Element 4: wherein the at least one additional optical thin film layer is made of a material selected from the group consisting of an oxide, a nitride, a carbide, and any combination thereof. Element 5: wherein the at least one additional optical thin film layer is doped to achieve the third refractive index. Element 6: wherein two or more materials are combined to achieve the third refractive index. Element 7: wherein the at least one additional optical thin film layer is made of a liquid or a gas. Element 8: wherein the first refractive index is greater than the second refractive index and the third refractive index is greater than the first refractive index. Element 9: wherein the first refractive index is greater than the second refractive index and the third refractive index is less than the second refractive index. Element 10: wherein the first refractive index is greater than the second refractive index and the third refractive index is a value between the first and second refractive indices.

Element 11: wherein the at least one additional optical thin film layer interposes corresponding optical thin film layers of the first and second pluralities. Element 12: wherein the at least one additional optical thin film layer is a terminal layer deposited on an end of the thin film stack opposite the substrate. Element 13: wherein the at least one additional optical thin film layer is doped to achieve the third refractive index. Element 14: wherein two or more materials are combined to achieve the third refractive index.

Element 15: wherein depositing the at least one additional optical thin film layer in or on the thin film stack comprises depositing the at least one additional optical thin film layer between corresponding optical thin film layers of the first and second pluralities. Element 16: wherein depositing the at least one additional optical thin film layer in or on the thin film stack comprises depositing the at least one additional optical thin film layer on an end of the thin film stack opposite the substrate. Element 17: wherein the first refractive index is greater than the second refractive index and the third refractive index is greater than the first refractive index or less than the second refractive index. Element 18: wherein the first refractive index is greater than the second refractive index and the third refractive index is a value between the first and second refractive indices.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An integrated computational element, comprising:
   an optical substrate;
   pluralities of first and second optical thin film layers alternatingly deposited on the optical substrate to form a thin film stack, wherein each first optical thin film layer exhibits a first refractive index and each second optical thin film layer exhibits a second refractive index different than the first refractive index; and
   at least one additional optical thin film layer arranged in or on the thin film stack and in optical communication with at least one of the first and second optical thin film layers, the at least one additional optical thin film layer exhibiting a third refractive index that is different than the first and second refractive indices, wherein the integrated computational element with the additional optical thin film layer is configured to modify an electromagnetic radiation interacted with a sample substance to have an intensity proportional to a characteristic of the sample substance.

2. The integrated computational element of claim 1, wherein the at least one additional optical thin film layer is placed in the thin film stack between a first optical thin film layer and a second optical thin film layer.

3. The integrated computational element of claim 1, wherein the at least one additional optical thin film layer is placed on the thin film stack as a terminal layer deposited opposite the optical substrate.

4. The integrated computational element of claim 1, wherein the at least one additional optical thin film layer is made of a material selected from the group consisting of silicon (Si), quartz ($SiO_2$), $SiO_X$, niobia and niobium, germanium and germania, MgF, zinc oxide, aluminum oxide, titanium oxide, tantalum, tantalum oxide, low index fluoropolymers, and high index nano-particle filled polymers.

5. The integrated computational element of claim 1, wherein the at least one additional optical thin film layer is made of a material selected from the group consisting of an oxide, a nitride, a carbide, and any combination thereof.

6. The integrated computational element of claim 1, wherein two or more materials are combined to achieve the third refractive index.

7. The integrated computational element of claim 1, wherein the at least one additional optical thin film layer is doped to achieve the third refractive index.

8. The integrated computational element of claim 1, wherein the at least one additional optical thin film layer is made of a liquid or a gas.

9. The integrated computational element of claim 1, wherein the first refractive index is greater than the second refractive index and the third refractive index is greater than the first refractive index.

10. The integrated computational element of claim 1, wherein the first refractive index is greater than the second refractive index and the third refractive index is less than the second refractive index.

11. The integrated computational element of claim 1, wherein the first refractive index is greater than the second refractive index and the third refractive index is a value between the first and second refractive indices.

12. An optical computing device, comprising:
a light source configured to emit electromagnetic radiation that optically interacts with a substance and an integrated computational element (ICE) core and thereby generate optically interacted light, the ICE core comprising:
an optical substrate;
pluralities of first and second optical thin film layers alternatingly deposited on the optical substrate to form a thin film stack, wherein each first optical thin film layer exhibits a first refractive index and each second optical thin film layer exhibits a second refractive index different than the first refractive index; and
at least one additional optical thin film layer arranged in or on the thin film stack and in optical communication with at least one of the first and second optical thin film layers, the at least one additional optical thin film layer exhibiting a third refractive index that is different than the first and second refractive indices, wherein the integrated computational element with the additional optical thin film layer is configured to modify an electromagnetic radiation interacted with a sample substance to have an intensity proportional to a characteristic of the sample substance; and
at least one detector arranged to receive the optically interacted light and generate an output signal corresponding to the characteristic of the sample substance.

13. The optical computing device of claim 12, wherein the at least one additional optical thin film layer is placed in the thin film stack between a first optical thin film layer and a second optical thin film layer.

14. The optical computing device of claim 12, wherein the at least one additional optical thin film layer is placed on the thin film stack as a terminal layer deposited opposite the optical substrate.

15. The optical computing device of claim 12, wherein the at least one additional optical thin film layer is made of a material selected from the group consisting of silicon (Si), quartz ($SiO_2$), $SiO_x$, niobia and niobium, germanium and germania, MgF, zinc oxide, titanium oxide, low index fluoropolymers, and high index nano-particle filled polymers.

16. The optical computing device of claim 12, wherein the at least one additional optical thin film layer is doped to achieve the third refractive index.

17. The optical computing device of claim 12, wherein the at least one additional optical thin film layer comprises two or more materials combined to achieve the third refractive index.

18. A method of fabricating an integrated computational element, comprising:
alternatingly depositing pluralities of first and second optical thin film layers on an optical substrate and thereby forming a thin film stack, wherein each first optical thin film layer exhibits a first refractive index and each second optical thin film layer exhibits a second refractive index different than the first refractive index;
selecting a third refractive index and a thickness of at least one additional optical thin film layer according to a regression vector for a characteristic of a substance, wherein the integrated computational element with the at least one additional optical thin film layer is configured to modify an electromagnetic radiation interacted with a sample substance to have an intensity proportional to a characteristic of the sample substance; and
depositing the at least one additional optical thin film layer in or on the thin film stack and in optical communication with at least one of the first and second optical thin film layers.

19. The method of claim 18, wherein depositing the at least one additional optical thin film layer in or on the thin film stack comprises depositing the at least one additional optical thin film layer between a first optical thin film layer and a second optical thin film layer.

20. The method of claim 18, wherein depositing the at least one additional optical thin film layer in or on the thin film stack comprises depositing the at least one additional optical thin film layer on an end of the thin film stack opposite the optical substrate.

21. The method of claim 18, wherein the first refractive index is greater than the second refractive index and the third refractive index is greater than the first refractive index or less than the second refractive index.

22. The method of claim 18, wherein the first refractive index is greater than the second refractive index and the third refractive index is a value between the first and second refractive indices.

* * * * *